(12) United States Patent
Liu et al.

(10) Patent No.: US 6,371,944 B1
(45) Date of Patent: Apr. 16, 2002

(54) PERCUTANEOUS NEEDLE WITH ENTRY FOR INSERTION OF A WIRE

(76) Inventors: Xuanli Liu, 15017, 61 Rd, Flushing, NY (US) 11367; Yuenian E. Shi, 18 Yale St., Roslyn Heights, NY (US) 11577

( * ) Notice: Subject to any disclaimer, the term of this patent is extended or adjusted under 35 U.S.C. 154(b) by 0 days.

(21) Appl. No.: 09/298,863

(22) Filed: Apr. 26, 1999

(51) Int. Cl.⁷ ............................................. A61M 25/00
(52) U.S. Cl. .................................................. 604/284
(58) Field of Search ............................... 604/181, 187, 604/188, 240–243, 284, 533

(56) References Cited

U.S. PATENT DOCUMENTS

| | | | |
|---|---|---|---|
| 5,273,533 A | * 12/1993 | Bonaldo | 604/83 |
| 5,290,242 A | * 3/1994 | Vaillancourt | 604/163 |
| 5,290,244 A | * 3/1994 | Moonka | 604/164 |
| 5,358,490 A | * 10/1994 | Henry et al. | 604/167 |
| 5,395,352 A | * 3/1995 | Penny | 604/256 |
| 5,507,732 A | * 4/1996 | McClure et al. | 604/280 |
| 5,603,706 A | * 2/1997 | Wyatt et al. | 604/283 |
| 5,613,954 A | * 3/1997 | Nelson et al. | 604/167 |
| 5,735,813 A | * 4/1998 | Lewis | 604/43 |
| 5,766,211 A | * 6/1998 | Wood et al. | 604/32 |
| 5,810,793 A | * 9/1998 | Boettger | 604/284 |

* cited by examiner

Primary Examiner—Sharon Kennedy
(74) Attorney, Agent, or Firm—Glenna Hendricks

(57) ABSTRACT

A needle is attached to a connector portion having a common passage with an an arm with a lumen that has a one-way valve which prevents flow of fluid from the needle through the lumen of the arm which acts as a conduit for insertion of a wire into the channel of the needle that has been inserted into a blood vessel. The connector portion having the arm may be provided as a separable adapter for use with a conventional needle hub or may be a part of the needle assembly.

4 Claims, 2 Drawing Sheets

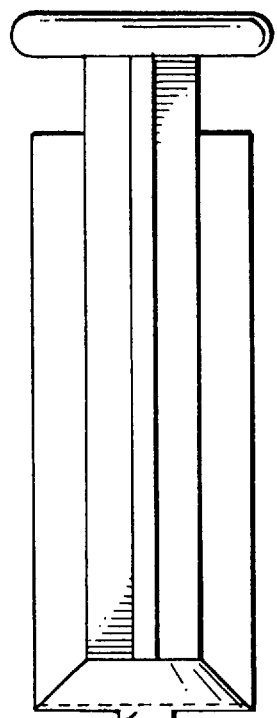
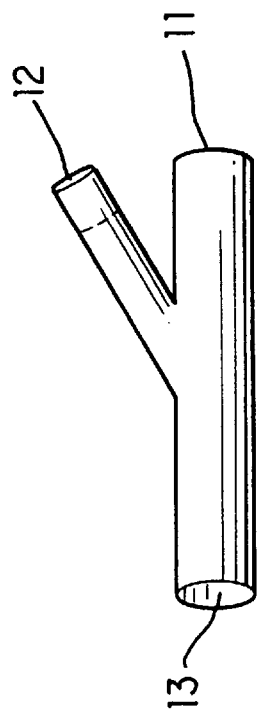
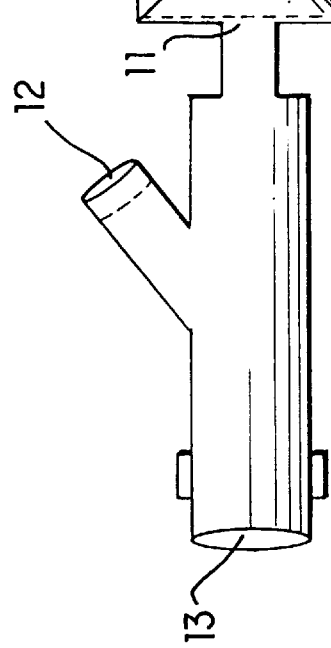
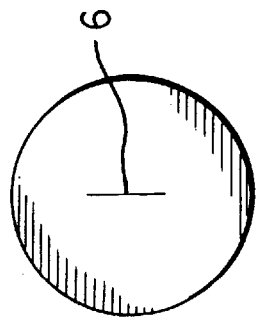
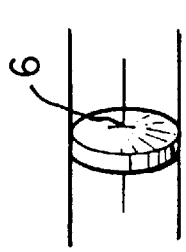

PERCUTANEOUS NEEDLE WITH ENTRY FOR INSERTION OF A WIRE

FIELD OF THE INVENTION

This invention relates to a percutaneous needle with a distal end portion which can be attached to a receptacle such as a syringe (called herein the connector portion). The connector portion has an arm with lumen which communicates with a common passage from the receptacle to the needle. The arm has a one-way valve which prevents flow of fluid from the needle through the arm which acts as a conduit for insertion of a wire into the channel of the needle that has been inserted into a blood vessel. The connector portion having the arm may be provided as a separable adapter for use with a conventional needle hub or may be a part of the needle assembly.

BACKGROUND OF THE INVENTION

Insertion of catheters and similar devices into the blood vessels for purposes of treatment or diagnosis plays a critical role in medical practice today. Present practices in radiology, in treatment and in diagnosis of cardiovascular disease, and in oncology and neurology require the entry of catheters into blood vessels. One of the more common uses of such catheters is in angioplasty wherein a balloon is inserted into the arterial vessel to dilate narrowed vessels. A guide wire is passed through a needle which has been inserted into the blood vessel. A catheter is then threaded on the guide wire into the blood vessel. Presently, after the needle is inserted into the blood vessel, the syringe is disassociated from the connector portion before the guide wire is inserted through the needle into the blood vessel. During this process, there is a considerable amount of bleeding from the connector portion of the needle assembly. Furthermore, the process requires at least two persons, since one person must remove the syringe from the connector portion of the apparatus while another inserts the wire through the lumen of the needle.

Many devices for multiple-purpose administration of fluids or medicaments and withdrawal of body fluids exist. However, they do not provide the means for entry of a guide wire through a needle into a blood vessel as does the invention disclosed herein. For example, U.S. Pat. No. 5,603,700, which is incorporated herein by reference in its entirety, discloses and claims a complex device for suctioning, for injecting fluids into the body and for disposing of various kinds of fluids from the body. The device is quite complex and would not be appropriate for use in admitting a guide wire into a blood vessel, especially into an artery.

Valves have been placed in the lumen of other devices. U.S. Pat. No. 4,946,449, which is incorporated herein by reference in its entirety, discloses a urethral catheter system having a mitral valve in a one-way passage which prevents flow of fluid from the bladder from flowing down-stream, but will allow fluid from down-stream to pass through the valve.

U. S. Pat. No. 5,542,933, which is incorporated herein by reference in its entirety, discloses and claims an apparatus having a valve for controlling flow of fluids through a conduit such as a catheter. The valve means is a block which obstructs the flow through the conduit as the block is adjusted. There is no passage for admission of a wire.

U.S. Pat. No. 5,827,218 teaches a suction pool tip having separate passages for irrigation liquid flow and for suctioned flow. Flow through these passages is controlled by valve plungers. The apparatus is not appropriate for use in inserting a guide wire through a needle.

Needle assemblies having an arm with a rubber septum which is penetrated by a needle for purposes of instilling medicaments through a needle are known. However, a septum is not appropriate for use with a guide wire, since the wire must, of necessity, have a flexible tip that will not damage a blood vessel. Such a wire is not sufficiently sharp or hard to insert though a septum, since a wire that would readily penetrate the septum would damage the blood vessel.

SUMMARY OF THE INVENTION

This invention provides a needle assembly comprising a needle portion and a connector portion, said connector portion having a first entry, a second entry, and a third entry, all entries leading to a common passage, said common passage being conical in shape, to provide means of guidance of a linear object inserted through said second entry toward said third entry, and wherein said first and said third entry are positioned approximately opposite each other while said second entry admits entrance to an arm which projects from the common passage at an angle of 20° to 60° from a line which would pass thought said first and second entries. The connector portion having the common passage may be separable from the needle portion.

BRIEF DESCRIPTION OF THE DRAWINGS

FIG. 2(a) and 2(b) show an adapter with three entries with 2(a) showing the connector portion as an adapter attached to a syringe and 2(b) showing the connector portion separate from the syringe.

DETAILED DESCRIPTION OF THE INVENTION

It is the purpose of this invention to provide a means for admitting a guide wire which may act as a guide for insertion of a catheter into a blood vessel through a previously-inserted needle without removing the syringe or other receptacle to which the needle is attached through the connector portion from the needle-receptacle assembly. The instant invention provides a needle (7) attached to a connector portion which is, or can be, attached to a receptacle such as syringe. The connector portion has an arm with a lumen or channel which acts as a conduit from the exterior environment into the needle portion (7) which provides means for entering into a blood vessel. The channel of the arm is divided by a valve (5) so that fluid (blood) flowing through the needle and common passage can not escape through the distal entry of the arm. Though the valve prevents flow of blood back through distal end of the arm, it will allow a guide wire to enter into the lumen of the needle already in place in the blood vessel. The apparatus may also consist of a needle with a conventional hub and a separable connector portion or adapter having three entries, said connector having a common conduit and which, when assembled for use, has a first entry into a receptacle, a second entry into an arm and a third entry into a conduit such as a needle wherein the arm is configured so that the proximal end of the channel or lumen of said arm communicates with a common passage from the receptacle and the needle or other conduit, said common passage having a conical shape so that it narrows in such a manner that a guide wire inserted into the second entry is readily guided toward the narrow segment of the cone toward the third entry toward the needle.

Figure 1A:
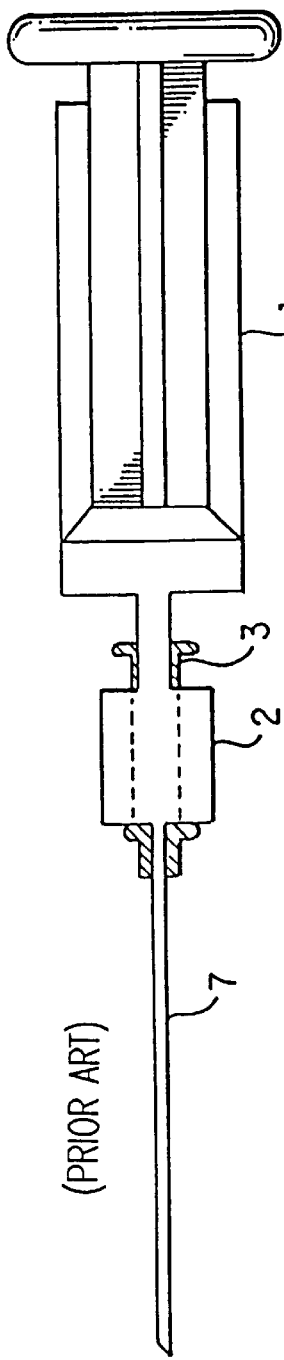
FIG. 1 shows, at 1(a), the presently used percutaneous entry needle and, at 1(b), the instantly claimed invention wherein there are three entries into a common passage, wherein one entry provides access to a needle. 1(c) shows a close-up of the connection system. 1(d) and 1(e) show the valve.
Figure 1B:
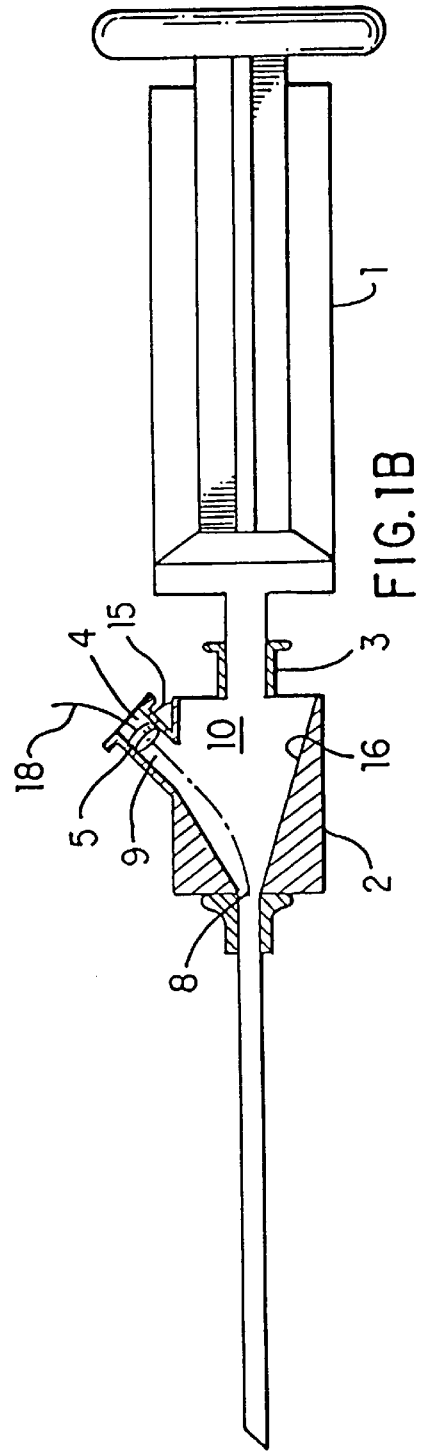
Figure 1C:
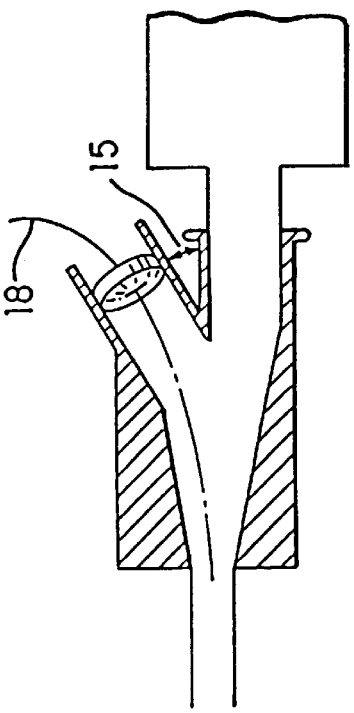

Referring the figures, FIG. 1(a) shows the prior art needle and adapter with a syringe. Referring to FIG. 1(b), which depicts aspects of the present invention, the assembled apparatus consists of a receptacle portion (1), such as a syringe, a connecting portion (2) having a common passage (10) from a first conduit to the receptacle portion, a first entry (3) for attachment to the receptacle portion of the apparatus and a second entry (4) into a second conduit (9) through which a flexible, linear object such as a guide wire can be inserted into and through the lumen of a conduit such as a needle and wherein the second entry has a one-way valve (5), such as a flap valve, which prevents backup of fluids such as blood through said second entry. The third entry (8) opens to the first conduit such as a needle that is inserted into the blood vessel. FIG. 1(c) shows an embodiment wherein the connecting portion containing the first, second and third entry are an integral part of a needle assembly appropriate for insertion into a blood vessel. FIG. 1(d) shows the valve (5) and a valve opening (6). The second conduit (9) extends at an angle (15) of about 20° to 60°, preferably about 25° to 45°, in relation to the a line drawn through the center of the passage leading from the syringe to the needle or first conduit. When the first conduit or needle has been inserted into the blood vessel the valve prevents blood from flowing out of the second entry. The connecting portion has a common passage (10) with an over-all cone-like shape to facilitate appropriate guidance of the wire (18) toward the lumen of the first conduit. The slant which forms the conical shape of the inside of the common passage is at an angle (16) of about 15° to 45° (preferably 20° to 40°) from a line parallel with a Line which would pass through the common passage from needle (the longitudinal axis) and into the receptacle such as a syringe. The smaller the angle identified by number 15, the easier it is to project a second conduit or wire through the common passage (10) and into the needle.

The instant invention provides distinctive improvements over the prior art. Consider, for example, the instance when the first conduit is a needle that is inserted into the blood vessel and the receptacle portion is a syringe. When the usual needle with connector is used, there is usually a considerable amount of blood which flows out through the passage which leads to the syringe when the syringe is disconnected from the needle connector portion in order to insert a guide wire. This is particularly true if the needle has been placed in an artery. It is usually necessary to have a second person available during this transfer to minimize loss of blood after the syringe has been removed and during the time the guide wire is being inserted into the needle. The instant apparatus allows the insertion of the wire without disconnecting the syringe, thus protecting the medical personnel from exposure to the blood of the patient. Using the device as taught, it is possible to minimize exposure of both the patient and the care-giver to infections.

Referring to FIG. 2(a) and 2(b), it is possible to use the invention by means of a separate adapter having three entries, a first entry for attachment to a receptacle such as a syringe (11), a second entry into the adapter which comes in at a slant (12) and a third entry (13) for connection to a first conduit. Using the separate adapter, the method of the invention may be practiced using standard equipment such as needles, syringes, catheters and wires found in most health care facilities.

The needles and adapters of the invention may be made of any of the materials used in production of such equipments, including glass, plastics, metals, elastomer or rubber. The properties required with depend on the intended use of the equipment.

What is claimed is:

1. A needle assembly with a needle portion and a connector portion, said connector portion having a first entry, a second entry, and a third entry, all entries leading to a common passage, said common passage being conical in shape, said conical shape resulting from a slant of the interior wall of said passage which differs from a longitudinal axis to provide means of guidance of a linear object inserted through said second entry though a conduit equipped with a one-way valve, wherein a wire passing though said second entry passes through said valve toward said third entry, and wherein said first and said third entry are positioned approximately opposite each other while said conduit entered through said second entry forms an arm which enters at an angle of from 20° to 60° from a line (longitudinal axis) which would pass thought said first and second entries.

2. An assembly of claim 1 comprising a connector portion which is fixedly attached, at the third entry to a needle.

3. An assembly of claim 1 wherein, at the first entry, there is attached a syringe.

4. An assembly of claim 1 wherein the valve is a mitral valve.

* * * * *